Figure 1:
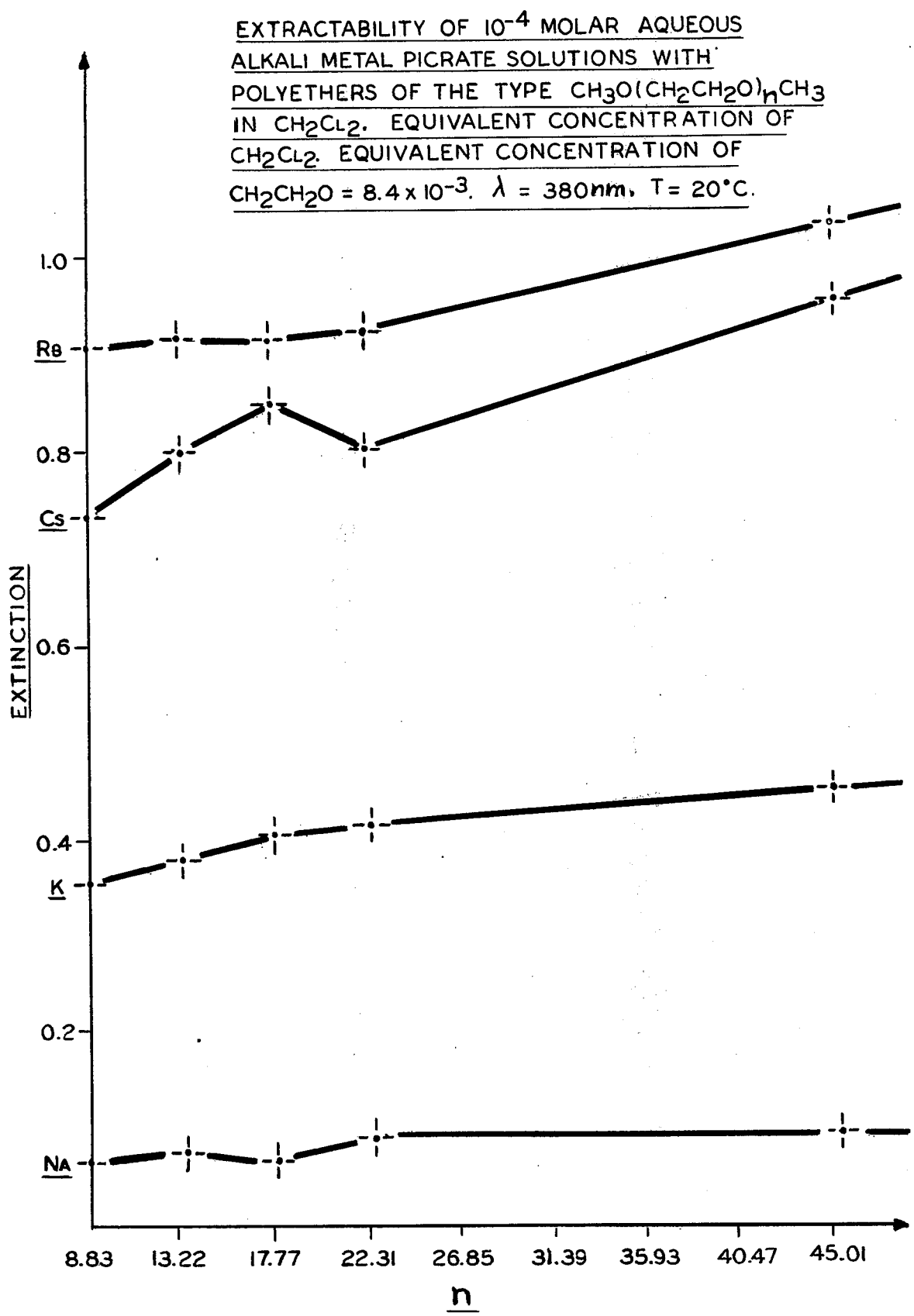

United States Patent [19]

Lehmkuhl et al.

[11] 4,113,649
[45] Sep. 12, 1978

[54] METHOD FOR THE SOLUBILIZING OF ALKALI METAL SALTS WITH POLYETHYLENEGLYCOLDIETHERS AND THE UTILIZATION THEREOF

[75] Inventors: Herbert Lehmkuhl, Mülheim, Germany; Farroch Rabet, Tehran, Iran

[73] Assignee: Studiengesellschaft Kohle mbH, Mulheim an der Ruhr, Germany

[21] Appl. No.: 711,742

[22] Filed: Aug. 4, 1976

[30] Foreign Application Priority Data

Aug. 5, 1975 [DE] Fed. Rep. of Germany ....... 2534851

[51] Int. Cl.$^2$ ............................................. B01F 3/00
[52] U.S. Cl. ................................. 252/363.5; 252/351; 252/188; 252/DIG. 14
[58] Field of Search ..................... 252/363.5, 351, 188, 252/DIG. 14

[56] References Cited

U.S. PATENT DOCUMENTS 3,684,707  8/1972  Livingston ........................ 252/363.5

OTHER PUBLICATIONS

Canadian Journal of Chemistry, vol. 53, 1975, pp. 2240–2246, Chaput et al.

*Primary Examiner*—Stephen J. Lechert, Jr.
*Attorney, Agent, or Firm*—Burgess, Dinklage & Sprung

[57] ABSTRACT

Process of solubilizing alkali- and alkali-earth metal salts, characterized in that the salts are reacted in the presence of solvents if desired, with open-chain polyethyleneglycoldiethers of the general formula

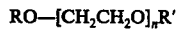

RO—[CH$_2$CH$_2$O]$_n$R' wherein $n = 6$ or more and R and R' are identical or different and represent alkyl, aryl or cycloalkyl groups respectively, the polyethyleneglycoldiethers having at least 7 oxygen atoms which are separated from one another each by two carbon atoms. The process can also be used to dissolve alkali metals.

14 Claims, 5 Drawing Figures

EXTRACTABILITY OF $10^{-4}$ MOLAR AQUEOUS POTASSIUM PICRATE SOLUTION WITH $10^{-3}$ MOLAR SOLUTIONS OF POLYETHER OF THE TYPE $CH_3O(CH_2CH_2O)_n CH_3$ IN $CH_2Cl_2$.

METHOD FOR THE SOLUBILIZING OF ALKALI METAL SALTS WITH POLYETHYLENEGLYCOLDIETHERS AND THE UTILIZATION THEREOF

BACKGROUND

Macrocyclic polyethers in which four to approximately twenty oxygen atoms are separated from one another each by two or more carbon atoms have in recent years aroused considerable interest in many fields of chemistry. They form stable complexes with alkali- and alkaline earth cations, in which the cation is surrounded by the oxygen atoms of the polyether macrocycle.

Through the formation of complexes with macrocyclic polyethers, inorganic salts can be made soluble in organic solvents in which they are normally virtually insoluble in the absence of the cyclic polyether. Organic salts complexed with cyclic polyethers—alkali picrates for example—can be extracted with organic solvents from aqueous solutions (see for example C. J. Pedersen and H. K. Frensdorff, Angew. Chem. 84, 16 (1972)). For example, even potassium permanganate or potassium tert.-butanolate dissolve in aromatic solvents if macrocyclic polyethers of suitable magnitude are added. Furthermore, the complexation of the cation greatly increases the dissociation of the ion pair between cation and anion. It is thus possible to increase the conductivity of salt solutions in organic solvents. Through the complexation of the cation and the shielding of the charge, highly reactive "naked" anions are formed, i.e., anions which are weakly or not at all complexed, and which are being used increasingly for substitution reactions.

It is assumed that the special effect of the cyclic polyethers is based on the fact that the cation is received into a polar, hydrophilic cavity of the ether molecule, while the exterior of the molecule is lipophilic. This effect is limited to cyclic compounds, and is known as the macrocyclic effect (B. Dietrich, J.-M. Lehn and J. P. Sauvage, Chemie in unserer Zeit 7, 120 (1973)). It is in harmony with this that, in comparative experiments with the open-chain oligoethers diglyme ($CH_3OCH_2CH_2OCH_2CH_2OCH_3$) and triglyme ($CH_3OCH_2CH_2OCH_2CH_2OCH_2CH_2OCH_3$), the alkali picrate extraction from aqueous phase by means of an organic solvent cannot be performed. (F. Vögtle and E. Weber, Angew. Chem. 86, 896 (1974), W. Wehner and F. Vögtle, Chem. Exp. Didakt. 1, 77 (1975)).

THE INVENTION

It has been found, quite surprisingly, that open-chain polyethyleneglycoldiethers of the general formula

RO($CH_2CH_2O$)$_n$R' having at least 7 oxygen atoms separated from one another each by 2 carbon atoms, and in which $n = 6$ and up, and R and R' are the same or different and represent alkyl, aryl or cycloalkyl terminal groups, exhibit properties with regard to the solubilizing of inorganic and organic salts, if desired in a solvent, e.g. an organic solvent, making available of very reactive anions from the salts, and for the dissolution of alkali metals, which are similar to those of the macrocyclic ethers, and often even superior thereto. $n$ can be, for example, 6–50, preferably 6–45.

R and/or R' can be branched and unbranched alkyl moieties having 1 to 20, preferably 1 to 15 carbon atoms, such as for example methyl, ethyl, n-propyl, sec. propyl, n-butyl, isobutyl, sec. butyl, tert. butyl, pentyl, octyl, decyl, dodecyl, 2-ethylhexyl etc.

R and/or R' can furthermore be cyclohexyl moieties having 3 to 15 carbon atoms, preferably having 5 to 12 carbon atoms, e.g., cyclopentyl, cyclohexyl, cycloheptyl, cyclooctyl, cyclodecyl, and cyclododecyl.

R and/or R' can be aryl moieties having 6 and more than 6 carbon atoms, e.g., phenyl, tolyl, mesityl, naphthyl, etc. It can be mononuclear or polynuclear having up to e.g. 3 nuclear moieties.

Figure 2:
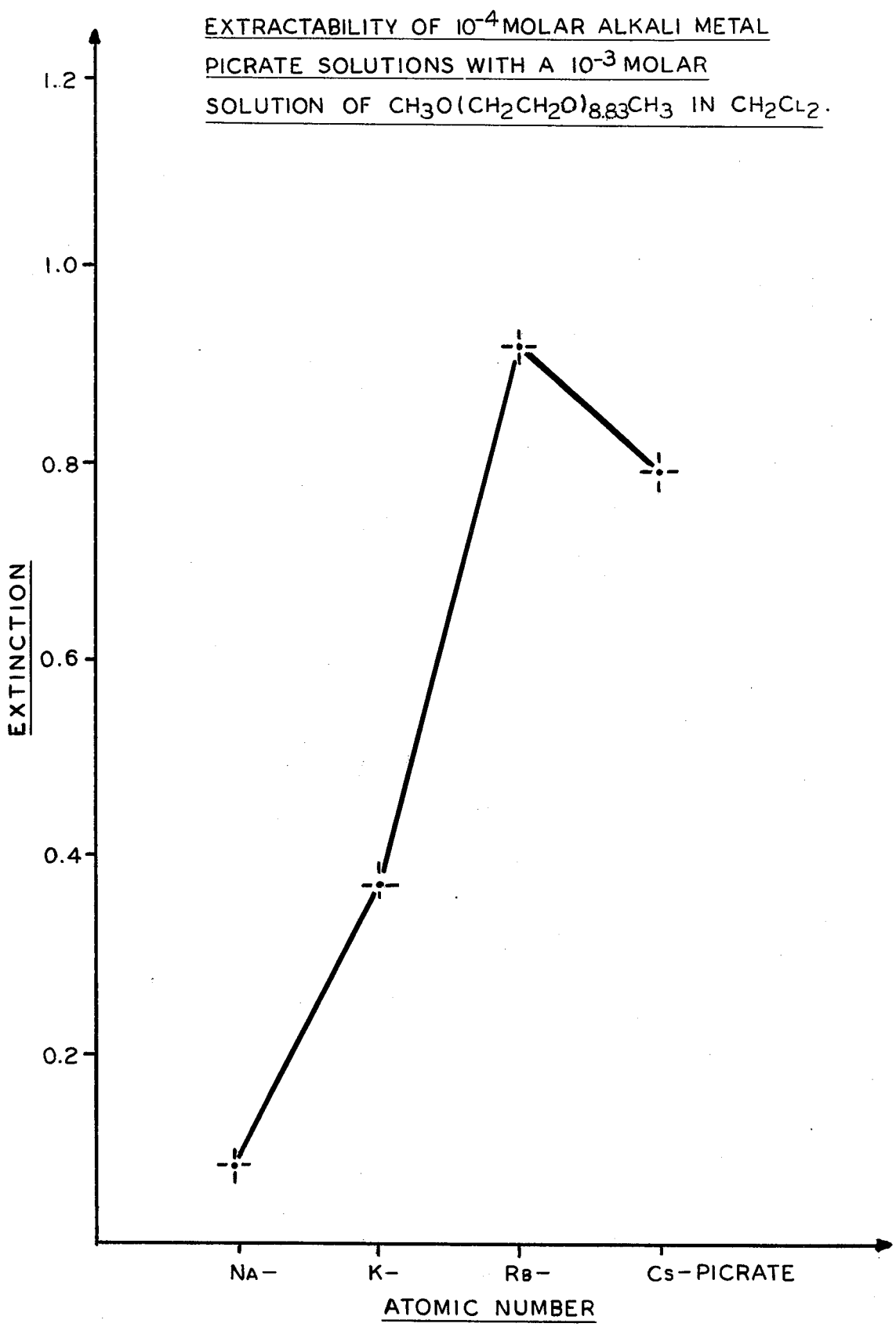
Figure 3:
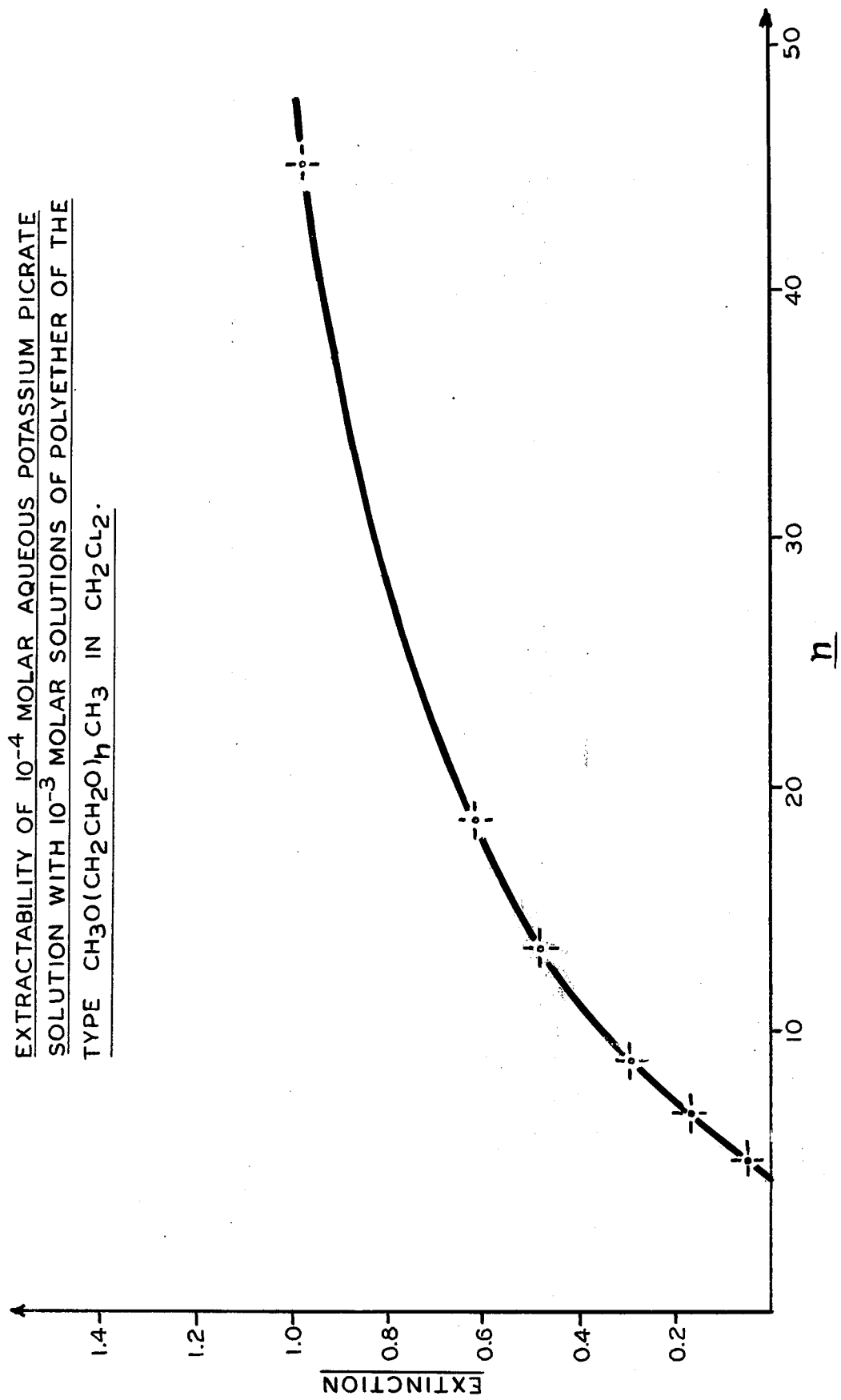
Figure 4:
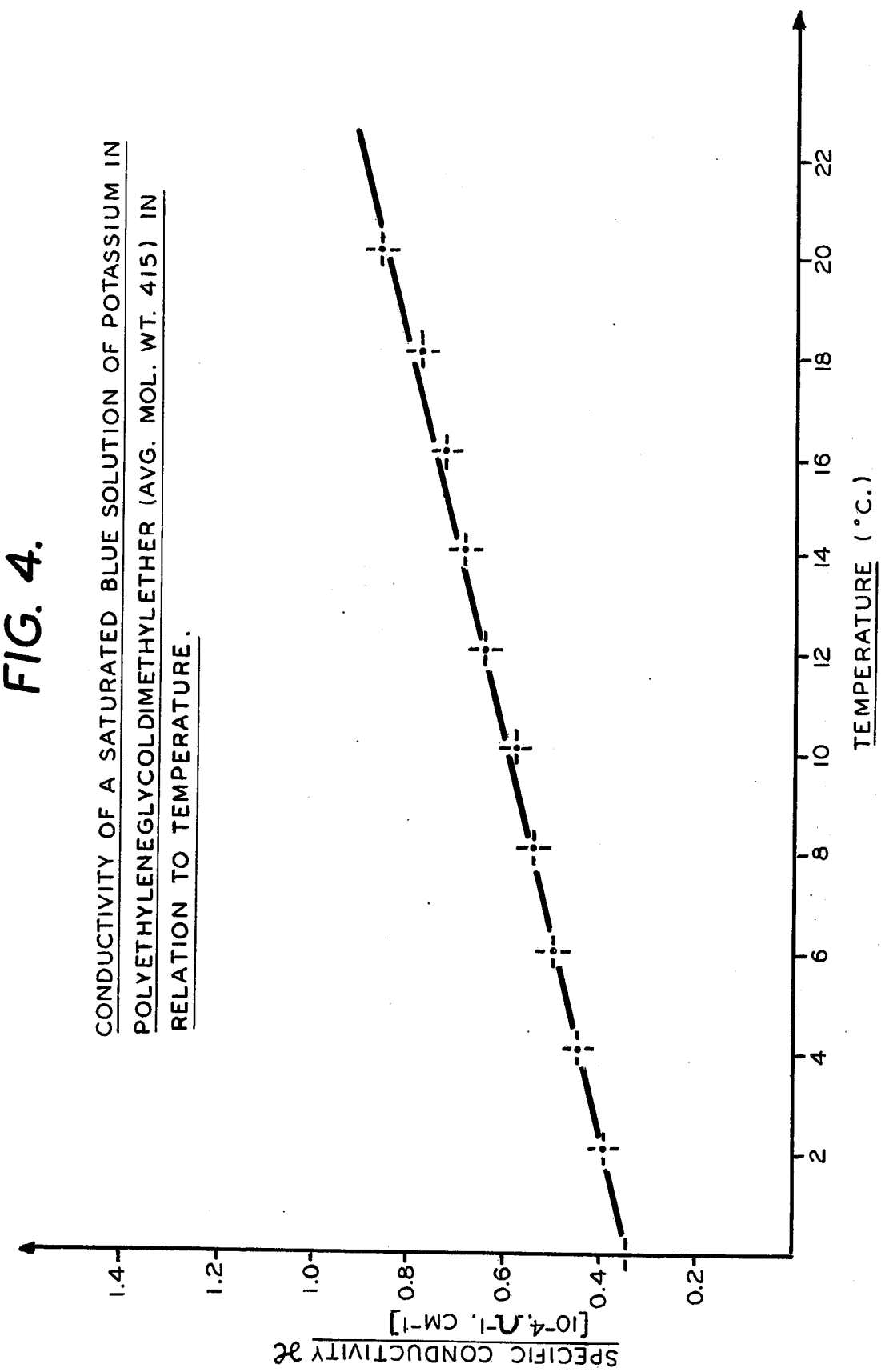
Figure 5:
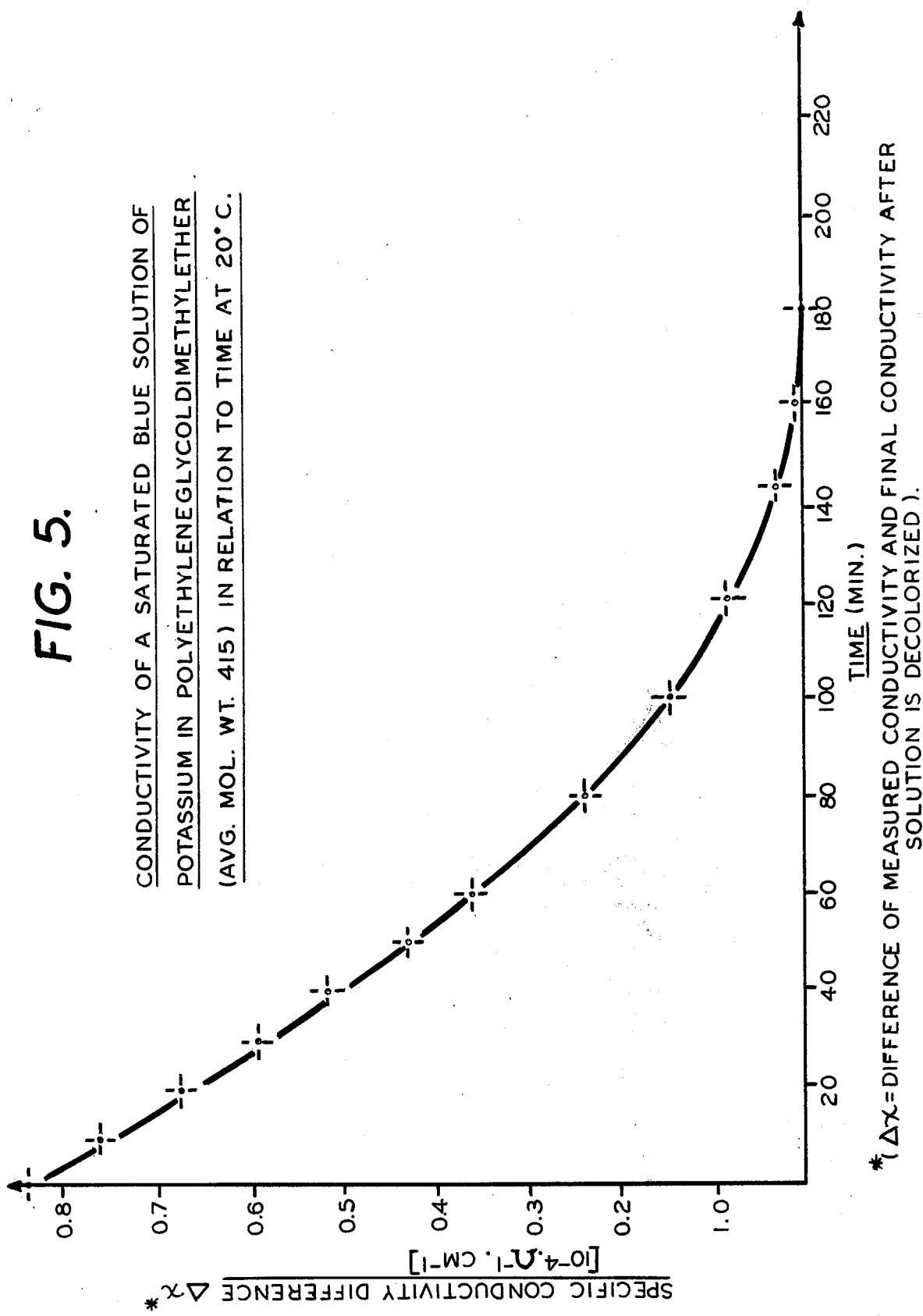

FIGS. 1, 2 and 3 are extraction curves for picrate solutions using polyethers for the extraction; and FIGS. 4 and 5 are conductivity curves for solutions of potassium in polyethers.

The polyethyleneglycoldiethers of the above formula which are used in accordance with the invention are, for example heptaethyleneglycoldimethylether, octaethyleneglycoldimethylether, octaethyleneglycolmethylethylether, heptaethyleneglycoldidodecylether, decaethyleneglycolmethyldodecylether, dodecaethyleneglycolethylphenylether, and also mixtures of diethers of suitable average molecular weight, such as, for example, polyethyleneglycoldimethylethers (average molecular weight 415, $n = 8.39$), polyethyleneglycoldodecylmethylethers (average molecular weight 569, $n = 8.39$), polyethyleneglycoldimethylethers (average molecular weight 1000, $n = 21.7$).

The alkali salts are common organic and inorganic alkali salts of, for example, lithium, sodium, potassium, rubidium and cesium, such as, for example, alkali metal salts of fatty acids, alcohols etc., and alkali metal salts of acids containing halogen, nitrogen, phosphorus and sulfur.

It is also possible to use alkaline earth metal salts of the above-mentioned kind, such as, for example, salts of beryllium, magnesium, calcium, strontium and barium.

By the addition of di- or triethylenglycoldialkyl ether to methylene chloride ($10^{-3}$M) it is not possible to extract potassium picrate from the aqueous solution ($10^{-4}$M). Upon the addition of polyethyleneglycoldialkyl ether containing at least 7 oxygen atoms, the extraction is successful (see FIGS. 1, 2 and 3). Furthermore, it can be seen from FIGS. 1 and 2 that, as the atomic number of the alkali metal increases from sodium to rubidium, the extractability of the alkali metal picrates increases, but then decreases slightly towards cesium. From FIG. 3 it can be seen that the extractability of potassium picrate is nil if $n$ is equal to or less than 5.

It has also surprisingly been found that the solubility of organic alkali metal salts in open-chain polyethyleneglycoldiethers of the type

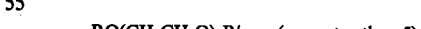

RO($CH_2CH_2O$)$_n$R'    ($n$ greater than 5)

is not only extraordinarily great—for example, 1.53 moles of potassium picrate dissolve in 1 liter of $CH_3O(CH_2CH_2O)_nCH_3$ having an average molecular weight of 415 ($n = 8.39$) at 20° C.—but also that the solubility greatly decreases as the temperature increases in the range from about 50° C. to about 200° C. The invention particularly contemplates conducting the dissolving step at −20°−+80° C., preferably −10°−+50° C.

In the case of the use of the macrocyclic polyethers, the recovery of the ether, i.e., the cleaving of the salt-ether complexes to their components, is impossible or is possible only with great difficulty. The effect of the decreasing solubility of salts as the temperature increases, which is seen in the case of open-chain polyethyleneglycoldiethers, and is at first surprising, can be understood on the basis of the conformative mobility of the open-chain polyether in contrast to the more rigid macrocyclic ethers. It is possible to make use of this advantageous effect for the separation of salt and complexing agents by heating. A solution saturated at room temperature of potassium acetate in benzene, if polyethyleneglycoldimethylether (average molecular weight 415 ($n = 8.39$)) is added, will reseparate a large part of the dissolved potassium acetate upon being heated at 70° to 80° C. When it is cooled back again to room temperature, all of the potassium acetate will go back into solution.

The polyethyleneglycoldiethers of the type

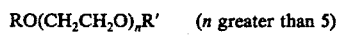
$RO(CH_2CH_2O)_nR'$    (n greater than 5)

can be used with extraordinary success for the preparation of highly concentrated solutions of alkali metal salts of organic dyes. A series of organic alkali salts dissolves in these ethers: alkali metal alcoholates, e.g., lithium-2-ethylhexanolate, potassium tert.-butanolate, sodium sec.-propanolate, lithium n-butanolate, and alkali phenolates such as lithium, sodium, potassium, rubidium and cesium phenolate; alkali metal salts of fatty acids, such as sodium acetate, potassium acetate, lithium propionate, rubidium stearate and sodium succinate; alkali metal salts of organic sulfonic acids, such as the lithium, sodium, potassium, rubidium or cesium salts of the sulfophthaleins.

In addition, the solubility and the conductivity even of inorganic salts in organic solvents can be substantially increased. For example, potassium bromide is only sparingly soluble in ethanol, and the specific conductivity of such a solution saturated at room temperature (approximately 0.025 mole/liter) is $0.25 \cdot 10^{-3} \omega^{-1} cm^{-1}$.

Upon the addition of polyethyleneglycoldimethylether (average molecular weight 1000 ($n = 21.7$)), the solubility and conductivity increase: see Table 1. This solution can be used as electrolyte for the preparation of transition metal alkoxides.

Table 1

Specific conductivities of KBr solutions in ethanol upon the addition of polyethyleneglycoldimethylether (avg. mol. wt. 1000 (n = 21.7)) (Amount added: 342 g of ether per liter); 209° C

| Conc. KBr in ethanol (mmol/l) | Specific conductivity $(\Omega^{-1}cm^{-1})$ |
|---|---|
| 46.1 | $1.19 \cdot 10^{-3}$ |
| 106.7 | 1.94 |
| 157.6 | 2.57 |
| 208.4 | 3.10 |
| 258.1 | 3.67 |
| Saturated solution (approximately 300) | 3.98 |

One very important application is the use of open-chain polyethyleneglycoldiethers as catalysts in substitution reactions. In the complexation of the cations by the polyethers, the anions formerly linked to the cations are largely released and display an extraordinarily high reactivity, since their charge is substantially shielded either by ion pair interaction or by solvatation. Typical applications are exchange reactions of bromide groups against acetate by means of potassium acetate, or bromide moieties against cyanide groups by means of potassium cyanide, of bromide groups against fluoride by means of potassium fluoride, or the exchange of bromide against iodide by means of potassium iodide.

Other reagents for such substitution reactions are lithium acetate, sodium propionate, sodium succinate, lithium cyanide, rubidium rhodanide, lithium iodide and potassium hydrogen sulfide.

Table 2 contains some typical experimental results, and shows the decisive action of the polyethyleneglycol diethers in contrast to uncatalyzed experiments.

Table 2

Conditions, products and transformation in the polyether-catalyzed reaction of benzyl bromide with various salts.

Salt : Benzyl bromide : Polyether ratio = 2 : 1 : 0.05

| Salt | Solvent | Reaction Time h | Reaction Temp. °C | Product | Transformation % | Polyether added |
|---|---|---|---|---|---|---|
| KHS | Benzene | 0.25 | 20 | PhCH$_2$SH | 100 | Ether 415[a] |
| KHS | Benzene | 0.25 | 20 | PhCH$_2$SH | <20 | none |
| KSCN | Benzene | 1 | 20 | PhCH$_2$SCN | 93 | Ether 415 |
| KSCN | Benzene | 2 | 20 | PhCH$_2$SCN | 100 | Ether 415 |
| KSCN | Benzene | 2 | 20 | — | 0 | none |
| KSCN | Acetonitrile | 2 | 20 | PhCH$_2$SCN | 100 | Ether 415 |
| KSCN | " | 2 | 20 | PhCH$_2$SCN | 100 | none |
| KN$_3$ | Benzene | 8 | 20 | PhCH$_2$N$_3$ | 100 | Ether 415 |
| KN$_3$ | Benzene | 2 | 20 | PhCH$_2$N$_3$ | 61 | Ether 415 |
| KN$_3$ | Benzene | 20 | 80 | PhCH$_2$N$_3$ | 14 | none |
| KN$_3$ | Acetonitrile | 2 | 20 | PhCH$_2$N$_3$ | 100 | Ether 415 |
| KN$_3$ | " | 2 | 20 | PhCH$_2$N$_3$ | 100 | none |
| K acetate | Benzene | 8 | 80 | PhCH$_2$OCOCH$_3$ | 100 | Ether 415 |
| K acetate | Acetonitrile | 2 | 20 | PhCH$_2$OCOCH$_3$ | 99 | Ether 415 |
| K acetate | Acetonitrile | 2 | 20 | PhCH$_2$OCOCH$_3$ | 2 | none |
| KCN | Benzene | 2 | 20 | PhCH$_2$CN | 0 | Ether 415 |
| KCN | Acetonitrile | 2 | 20 | PhCH$_2$CN | 24 | Ether 415 |
| KCN | " | 24 | 20 | PhCH$_2$CN | 100 | Ether 415 |
| KOH | " | 10 | 83 | PhCH$_2$OH | 20 | Ether 415 |
| KOH | " | 24 | 83 | PhCH$_2$OH | 66 | Ether 415 |

Table 2-continued

Conditions, products and transformation in the polyether-catalyzed reaction of benzyl bromide with various salts.
Salt : Benzyl bromide : Polyether ratio = 2 : 1 : 0.05

| Salt | Solvent | Reaction Time h | Temp. °C | Product | Transformation % | Polyether added |
|------|---------|-----------------|----------|---------|------------------|-----------------|
| KF | " | 24 | 83 | PhCH$_2$F | 38 | Ether 415 |

$^{a)}$Ether 415: Polyethyleneglycoldimethylether of an average molecular weight of 415; n = 8.39

Table 3

Conditions and transformation in the reaction of benzyl bromide with potassium acetate to form benzyl acetate, upon the addition of various polyethers.

Conditions: Benzyl bromide concentration 2.27 moles l$^{-1}$; Salt : Benzyl bromide ratio = 2 : 1

| Reaction Time h | Temp. °C | Solvent | Transf. % | n | RO(CH$_2$CH$_2$O)$_n$R' R | R' | Concentration of polyglycol derivative (mole l$^{-1}$) |
|---|---|---|---|---|---|---|---|
| 2 | 20 | Acetonitrile | 58 | 8.4 | CH$_3$ | CH$_3$ | 0.11 |
| 2 | 20 | " | 56 | 8.4 | CH$_3$ | Si(CH$_3$)$_3$ | 0.11 |
| 2 | 20 | " | 82 | 8.4 | CH$_3$ | OCCH$_3$ ‖ O | 0.11 |
| 2 | 20 | " | 65 | 8.4 | CH$_3$ | nC$_{12}$H$_{25}$ | 0.13 |
| 2 | 20 | " | 90 | 8.4 | Ph | Ph | 0.13 |
| 2 | 20 | " | 100 | 22 | CH$_3$ | CH$_3$ | 0.13 |
| 24 | 20 | " | 0 | 8.4 | CH$_3$ | H | 0.13 |
| 2 | 20 | Benzene | 3 | 8.4 | CH$_3$ | CH$_3$ | 0.11 |
| 24 | 40 | " | 13 | 8.4 | CH$_3$ | CH$_3$ | 0.11 |
| 8 | 80 | " | 100 | 8.4 | CH$_3$ | CH$_3$ | 0.11 |
| 2 | 20 | Acetonitril | 100 | 45 | CH$_3$ | CH$_3$ | 0.11 |

Table 4

Oligoethyleneglycoldimethylether-catalyzed reaction of benzyl bromide with potassium azide to form benzyl azide at 80° C in benzene. Transformation after two hours.
Ratio of salt to benzyl bromide to ether = 2 : 1 : 0.05

| Ether | Transformation after 2 h | Reaction products |
|---|---|---|
| None | 0 | — |
| Diglyme (dried over NaAl(C$_2$H$_5$)$_4$ | 0 | — |
| CH$_3$O(CH$_2$CH$_2$O)$_n$CH$_3$ (n = 8.39) | 61 | Benzyl azide |

Table 5

Conditions, products and transformation of the reaction of n-octyl bromide with various salts, catalyzed by polyethylglycoldimethylether (M = 4 15, n = 8.4).

| Salt | Solvent | Reaction Time h | Temp. °C | Product | Transformation % | Ether added Moles $^{-1}$ |
|---|---|---|---|---|---|---|
| KI | H$_2$O | 3 | 100 | C$_8$H$_{17}$I | 44 | 0.8 |
| KI | H$_2$O | 3 | 100 | — | 0 | 0 |
| K acetate | Acetonitrile | 24 | 83 | C$_8$H$_{17}$OCOCH$_3$ | 99 | 0.36 |

Another advantage of the open-chain polyethers over the macrocyclic ethers is their availability.

In recent years a number of methods have been elaborated for the synthesis of cyclic polyethers, but they always involve a plurality of steps and usually achieve only moderate yields of desired product, so that the price of the commercial macrocyclic polyethers is extremely high, which is a great obstacle to their widespread use (C. J. Pedersen and H. K. Frensdorff, Angew. Chem. 84, 16 (1972)).

For the preparation of the open-chain polyethyleneglycoldialkylethers, one sets out from the polyethyleneglycolmonoethers which are produced industrially in large quantities, or from the polyethyleneglycols which are obtained by the polymerization of ethylene oxide. These substances can be either polyethyleneglycolmonoethers and polyethyleneglycols of uniform molecular size or mixtures of appropriate average molecular weight, such as the polyethyleneglycols of average molecular weights of 400, 600, 800, 1000 and 2000. The monoethers, or the diols as the case may be, can be transformed by conventional methods to the corresponding diethers. The reaction of monoether or diol with sodium hydride and methyl iodide (C. A. Brown and D. Barton, Organic Synthesis, June 1974, p. 434) or methyl chloride gives especially satisfactory results.

The potassium metal concentration in THF upon the addition of "cyclohexyl-18-krone-6" are given as 10$^{-4}$ molar (J. L. Dye, M. G. Debacker, V. A. Nicely, J. Amer. Chem. Soc. 92, 5226 (1972)), and in diethyl ether as 10$^{-6}$ to 10$^{-7}$ molar (D. C. Dye and co-workers, Ber. Bunsengesellschaft Phys. Chem. 75, 659 (1971)). In diethyl ether, in the presence of cryptate

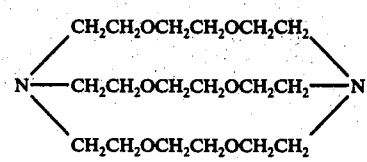

the potassium concentration increases to approximately 10$^{-4}$ molar. In the absence of macrocyclic ethers, the concentration of dissolved potassium in dimethoxyethane is 6–10 · 10$^{-4}$ molar, and in THF it is 3 to 5 · 10$^{-4}$ molar (F. S. Dainton, D. M. Wiles and A. N. Wright, J. Chem. Soc. 1960, 4283). Diglyme dissolves approximately 0.002% sodium.

In polyethyleneglycoldialkylethers of at least 7 oxygen atoms, the potassium solubility increases very greatly and attains levels of 0.5 molar; at the same time it is striking that the solutions are stable up to temperatures around 0°. Within one hour, the conductivity of a saturated solution of potassium in polyethyleneglycoldimethylether (average molecular weight 415, $n = 8.39$) remains unvarying at 3 to $3.1 \cdot 10^{-5} \omega^{-1} cm^{-1}$. The specific conductivity increases as the temperature increases (see FIG. 4), and upon long standing at a given temperature above $+10°$ C. it decreases as a result of decomposition (see FIG. 5). The open chain ethers of the invention can in general be used as the known macrocyclic ethers are used, with the modifications and improvements indicated herein.

EXAMPLES

EXAMPLE 1

Extraction of potassium picrate from aqueous solution with a mixture of methylene chloride and polyethyleneglycoldimethylether (avg. molecular weight 415, $n = 8.39$.)

(a) Preparation of the diether 4.4 grams (0.18 mole) of sodium hydride and 60 milliliters of tetrahydrofuran are placed under an argon atmosphere in a 250 ml two-necked flask equipped with reflux condenser and magnetic stirrer. The mixture is heated in an oil bath to about 50° C., and 17.0 g of $CH_3I$ (7.5 ml = 0.12 mole) is added slowly, drop by drop. Then 32 g (approx. 0.08 mole) of the polyether, dissolved in 30 ml of THF, is added over a period of 30 minutes, and while it is being added a strong formation of gas ($H_2$) is observed. (The volume of the hydrogen gas that forms corresponds to the stoichiometric amount.)

The mixture is stirred for another 60 minutes at 50° C. and at the end is brought briefly to a boil. The excess sodium hydride (as well as sodium iodide, if any) is filtered out, and the THF is completely drawn off. 250 ml of toluene is added to the residue, heated for 30 minutes up to the refluxing point, and filtered while hot. The toluene is then completely drawn off and the residue is purified either by molecular distillation at 200° C. and $10^{-3}$ Torr or by extraction with n-pentane. Yield 16.5 g (50%); average molecular weight (determined cryoscopically in benzene): 415 ($n = 8.39$).

(b) Extraction

For the extraction the following solutions are prepared: $10^{-4}$ molar sodium picrate, potassium picrate, rubidium picrate and cesium picrate solutions, each in their $10^{-1} \times$ normal hydroxide solutions in water. A $10^{-3} \times$ molar solution of polyethyleneglycoldimethylether in methylene chloride.

Equal volumes of the polyether solution and picrate solutions are combined and shaken until the extraction equilibrium is reached. The methylene chloride phase is separated, dried over $Na_2SO_4$, and the extinction at 380 nm is measured directly (see FIG. 2).

EXAMPLE 2

Determination of the solubility of potassium picrate in polyethyleneglycoldimethylether (average molecular weight 415, $n = 8.39$).

5 ml of polyether is treated with an excess amount of completely dry potassium picrate and stirred at room temperature for 8 hours with the exclusion of moisture. The yellow solution is filtered off. The potassium content determination shows a potassium picrate concentration of 1.53 moles per liter.

EXAMPLE 3

Determination of the conductivity of potassium bromide in an ethanol-polyethyleneglycoldimethylether (average molecular weight 1000, $n = 21.7$) solution.

549.2 mg of potassium bromide was added to 50 ml of absolute ethanol and stirred for a relatively long time at room temperature. The potassium bromide did not dissolve entirely. The specific conductivity of this solution was $$H = 0.25 \times 10^{-3} \Omega^{-1} cm^{-1}$$

Then 17.1 g of polyethyleneglycoldimethylether (average molecular weight 1000, $n = 21.7$) was dissolved in 50 ml of absolute ethanol and added to the above suspension. The potassium bromide dissolved clear, and the conductivity increased. By the addition of more portions of potassium bromide it was possible to obtain the conductivity values given in Table 1.

The conductivity of the saturated solution was:

$$H = 3.98 \times 10^{-3} \Omega^{-1} cm^{-1}$$

EXAMPLE 4

Temperature dependence of the solubility of potassium acetate-polyethyleneglycoldimethylether (average molecular weight 415, $n = 8.39$) in benzene.

Potassium acetate is added to a solution of 8 g of polyethyleneglycoldimethylether (average molecular weight 415, $n = 8.39$) in 25 ml of ethanol at 20° C. until all of the potassium salt will no longer dissolve. After separating the solution from the sediment, one removes the ethanol at 20° C. in a vacuum of approximately one Torr, adds 50 ml of benzene, stirs for 2 hours, and filters out the undissolved salt. The solution contains 0.103 moles per liter of potassium acetate at 20° C. If the clear solution is then heated at 80° C. (30 minutes), potassium acetate precipitates out. After the salt precipitate has been allowed to settle, the supernatant clear solution at 80° C. contains only 0.034 moles per liter of potassium acetate.

EXAMPLE 5

Preparation of Benzyl Acetate

In a 50 milliliter round flask 9.8 g (0.1 mole) of dry potassium acetate, 12.5 ml of acetonitrile and 1.1 g (0.0025 mole) of polyethyleneglycoldimethylether (average molecular weight 415, $n = 8.39$) are placed and stirred at room temperature with a magnetic stirrer for 30 minutes. Then 8.55 g (6.0 ml = 0.05 mole) of benzyl bromide is added. The mixture is then stirred for another two hours at room temperature. Then all volatiles are condensed out in a high vacuum of $10^{-3}$ Torr. Gas chromatographic and spectrometric coupling analysis (G.C.-M.S.) shows that a 100% transformation of benzyl bromide to benzyl acetate has taken place.

EXAMPLE 6

Preparation of Benzyl Cyanide 13 grams (0.2 mole) of dry potassium cyanide, 20 ml of acetonitrile, 1.7 g (0.004 mole) of polyethyleneglycoldimethylether (average molecular weight 415, $n = 8.39$) and 8.55 g (6.0 ml = 0.05 mole) of benzyl bromide are placed in a 50 ml round flask. The mixture is stirred for 24 hours at room temperature. Then all volatile components are condensed in a high vacuum at $10^{-3}$ Torr. G.C.-M.S coupling analysis shows that a 100% transformation of benzyl bromide to benzyl cyanide has taken place.

EXAMPLE 7

Preparation of n-Octyl Iodide

First a saturated solution of 41.5 g (0.25 mole) of potassium iodide in water is prepared. To this solution are added 4.2 g (0.001 mole) of polyethyleneglycoldimethylether (average molecular weight 415 ($n$ = 8.39)) and 9.65 g (0.05 mole) of n-octylbromide, and the mixture is heated with stirring until the onset of refluxing. After cooling, the organic phase is separated and the aqueous phase is washed twice with diethyl ether. The ethereal solution and the organic phase are combined, the ether is withdrawn, and then all volatile components are condensed at a high vacuum. G.C.-M.S. coupling analysis shows an octyl iodide yield of 44%. The cleavage of hydrogen halide from the octyl halide to form 1-octene, which is observed when cyclic polyether is used, occurs to only a slight extent (less than 1%).

EXAMPLE 8

Potassium solution in polyethyleneglycoldimethylether (average molecular weight 415 ($n$ = 8.39)).

The reaction vessels must be entirely free of moisture and oxygen. Consequently, before the reaction is started, the vessels are freed of moisture and air by repeated evacuation with heating, and filling with pre-dried argon.

20 ml of polyether was placed in a 50 ml two-necked flask. The flask was once again evacuated, filled with argon, and chilled to 0° C., and at this temperature a potassium-sodium alloy (K:Na = 4:1) was added in the argon stream. The blue solution formed upon the simple shaking of the flask. Within 30 minutes at 0° C., a dark blue solution developed, which was almost black in the greater depth.

The concentration of the solvatized electrons can best be determined by the amount of hydrogen formed in alcoholysis. A potassium concentration of 0.45 moles per liter was found.

The blue solution is immediately discolored by air. This blue solution can be used for electron transfer reactions, f.i. for the reduction of aromatic hydrocarbons and other unsaturated hydrocarbons.

EXAMPLE 9

In a manner similar to that described in Example 1, diethers can be prepared with different R and R' moieties. From 104 g of polyethyleneglycol-monododecylether — $C_{15}H_{25}(OCH_2CH_2)_7OH$, 11.1 g of NaH, 42.6 g of methyl iodide and 150 ml of THF, polyethyleneglycoldodecylmethylether is obtained in yields between 50 and 70%:

$C_{12}H_{25}(OCH_2CH_2)_7OCH_3$.

In the experiment described in Example 5, instead of the dimethyl ether, the dodecyl methyl ether is used in the amount of 1.3 g. Under otherwise identical conditions, a quantitative transformation of benzyl bromide to benzyl acetate again takes place.

EXAMPLE 10

In a manner similar to that described in Example 1, mixed diethers can also prepared having R and R' moieties in which R' is an aryl moiety. From 88 g polyethylene glycolmonophenylether $C_6H_5(OCH_2CH_2)_7OH$, 13.2 g of sodium hydride, 89.8 g of dodecyl bromide and 150 ml of THF, polyethyleneglycoldodecylphenylether—$C_{12}H_{25}(OCH_2CH_2)_7OC_6H_5$—is obtained in yields between 40 and 60%.

In the experiment described in Example 6, instead of the dimethyl ether, the dodecyl phenyl ether is used in a quantity of 1.5 grams. Under otherwise identical conditions, a quantitative transformation of benzyl bromide to benzyl cyanide takes place.

EXAMPLE 11

Instead of polyethyleneglycolether mixtures of an average molecular size, homogeneous compounds can also be prepared and used in accordance with the invention.

Heptaethyleneglycoldimethylether is prepared by the reaction of $CH_3OCH_2CH_2OCH_2CH_2Cl$ (carbitol chloride) with triethylene glycol is the presence of sodium hydride.

(a) Preparation of $CH_3OCH_2CH_2OCH_2CH_2Cl$

A mixture of 60 g of $CH_3OCH_2CH_2OCH_2CH_2OH$ (carbitol), 500 ml of benzene and 44 g of pyridine is brought to ebullition in a three-liter three-necked flask, and 66 g of thionyl chloride is added drop by drop over a period of 1½ hours. The mixture is refluxed for another 16 hours with constant stirring. After cooling, a solution of 5 ml of concentrated hydrochloric acid in 20 ml of water is added drop by drop over a period of 20 minutes. The benzene phase is then separated and dried over $Na_2SO_4$, the benzene is withdrawn, and the residue is fractionated in a water-jet vacuum (10 mm Hg).

Yield: 57 g = 82.6%; B.P. ($10^{-3}$ Torr) 53°-54° C.

(b) Preparation of heptaethyleneglycoldimethylether 4.6 g of NaH is suspended in 40 ml of absolute dioxane and a solution of 12.0 g of triethyleneglycol in 40 ml of dioxane is added drop by drop. The mixture is refluxed until the development of gas ($H_2$) has stopped. Then 27.7 g of carbitol chloride dissolved in 40 ml of dioxane is added drop by drop and the mixture is refluxed for 24 hours. The precipitated sodium chloride is separated and the dioxane is withdrawn.

Extraction of the residue with n-pentane yields heptaethyleneglycoldimethylether in an 84.3% yield.

Table 6

| Extractability of potassium picrate from a $10^{-4}$ molar aqueous solution with $10^{-3}$ molar solutions of $CH_3O(CH_2CH_2)_nOCH_3$ in $CH_2Cl_2$. | |
|---|---|
| n | Extinction ($\lambda$ = 380 nm, T = 20° C) |
| 7.0 | 0.165 |

What is claimed is:

1. Process of solubilizing a material which is an alkali metal, an alkali metal salt or an alkaline earth metal salt, which comprises contacting the material with open-chain polyethyleneglycoldiether of the formula

RO—[$CH_2CH_2O$]$_n$R' wherein $n$ = 6 or more and R and R' are identical or different and each is alkyl, aryl or cycloalkyl.

2. Process of claim 1, wherein said ether is contained in an organic solvent and increases the solubility of the material in the organic solvent.

3. Process of claim 1, wherein said ether is contained in an organic solvent and the conductivity in the solvent is increased by the material.

4. Process of claim 1, wherein the material is a salt and the ether containing the dissolved salt is contacted with a compound different from the salt for a substitution reaction between said dissolved salt and said compound.

5. Process of claim 1, wherein said material is an alkali metal.

6. Process of claim 1, wherein the material is dissolved in the ether at less than 60° C., and following dissolution of the material in the ether, the material is at least partially separated from the ether by heating to above 60° C.

7. Process of claim 5, wherein the heating is to 60°–250° C.

8. Process of claim 1, wherein the salt is an alkali metal salt.

9. Process of claim 1, wherein the salt is an alkaline earth metal salt.

10. Process of claim 1, wherein the salt is an organic salt.

11. Process of claim 1, wherein the salt is an organic alkali metal salt.

12. Process of claim 1, wherein $n$ is 7–45.

13. Process of claim 1, wherein $n$ is at least 7.

14. Process of claim 4, wherein said material is an alkali metal salt.

* * * * *

UNITED STATES PATENT AND TRADEMARK OFFICE
CERTIFICATE OF CORRECTION

PATENT NO. : 4,113,649
DATED : September 12, 1978
INVENTOR(S) : Herbert Lehmkuhl and Farroch Rabet It is certified that error appears in the above-identified patent and that said Letters Patent are hereby corrected as shown below:

Column 3, line 40, change "$\omega$" to --$\Omega$--.

Column 4, line 10, change "209°C" to --20°C--.

Column 5, line 46, change "415" to --4.15--.

Column 7, line 6, change "$\omega$" to --$\Omega$--.

Signed and Sealed this

Sixth Day of February 1979

[SEAL]

Attest:

RUTH C. MASON
Attesting Officer

DONALD W. BANNER
Commissioner of Patents and Trademarks